(12) United States Patent
Kokubo et al.

(10) Patent No.: US 8,021,690 B2
(45) Date of Patent: Sep. 20, 2011

(54) SOLID PREPARATION COATED WITH A FILM COATING LAYER AND FILM COATING AGENT

(75) Inventors: Hiroyasu Kokubo, Tokyo (JP); Sakae Obara, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 376 days.

(21) Appl. No.: 09/842,466

(22) Filed: Apr. 26, 2001

(65) Prior Publication Data

US 2001/0046517 A1    Nov. 29, 2001

(30) Foreign Application Priority Data

Apr. 26, 2000 (JP) ................................. 2000-125064
Jan. 26, 2001 (JP) ................................. 2001-018467

(51) Int. Cl.
*A61K 9/16* (2006.01)
*G03C 3/00* (2006.01)

(52) U.S. Cl. ........ 424/490; 424/489; 424/464; 424/474; 424/480; 424/467; 430/17

(58) Field of Classification Search .................. 424/490, 424/489, 464, 474, 480, 467; 118/624
See application file for complete search history.

(56) References Cited

U.S. PATENT DOCUMENTS

| | | | |
|---|---|---|---|
| 3,409,570 A * | 11/1968 | Dempski et. al. | |
| 4,478,658 A | 10/1984 | Wittwer | |
| 4,820,524 A * | 4/1989 | Berta | |
| 4,928,840 A | 5/1990 | Barshay et al. | |
| 5,089,270 A * | 2/1992 | Hampton et al. | ............. 424/465 |
| 5,464,631 A * | 11/1995 | Hoover et al. | |
| 5,511,361 A | 4/1996 | Sauter | |
| 6,406,738 B1 * | 6/2002 | Hogan et al. | |

FOREIGN PATENT DOCUMENTS

| | | |
|---|---|---|
| GB | 1041905 | 9/1966 |
| WO | WO 91/01884 | 2/1991 |

* cited by examiner

*Primary Examiner* — Robert A Wax
*Assistant Examiner* — Bethany Barham
(74) *Attorney, Agent, or Firm* — Alston & Bird LLP (57) ABSTRACT

The present invention provides solid preparations having two or more colors or a pattern of two or more different colors which can solve the problems of the prior art including the complexity of production processes and the low strength of solid preparations. Specifically, an object of the present invention is to provide solid preparations coated with a continuous film coating layer having two or more different colors or a pattern of two or more different colors which preparations are obtained by irradiating a part of the film coating layer containing one or more colorants with light, a process for the preparation of such solid preparations, and a film coating agent therefor. The present invention also provides a solid preparation treating apparatus for yielding a continuous film coating layer on the surface of a solid preparation with two or more different colors or a pattern of two or more different colors, which comprises a solid preparation loader movably disposed, a light controller for controlling the light-exposed surface area of the solid preparation and a light source for light irradiation.

24 Claims, 3 Drawing Sheets

SOLID PREPARATION COATED WITH A FILM COATING LAYER AND FILM COATING AGENT

BACKGROUND OF THE INVENTION

1. Field of the Invention

This invention relates to a solid preparation coated with a continuous film coating layer having two or more different colors or a pattern of two or more different colors wherein the preparation is obtained by, in the common film coating of tablets, irradiating a part of the film coating layer containing one or more colorants with light, a process for the preparation of such solid preparations, and a film coating agent therefor.

2. Description of the Related Art

There are various forms of solid preparations such as tablets, granules, powders and capsules, and they vary widely in size and shape. Among others, tablets and capsules are typical solid preparations which have been used for long. Tablets are popular because of excellent mass productivity, easy ingestibility and handy shape. Capsules are a dosage form which has no unpleasant taste, can be easily ingested, and hence gains the favor of most people. In some cases, pharmaceutical makers put capsules on the market in spite of the fact that the same medicines can be manufactured in the form of tablets.

Solid preparations referred to generically as capsules include hard capsules and soft capsules. The former is formed of gelatin or the like, and consists of a body and a cap. They can be fitted together to contain a medicine and the like therewithin. For purposes of identification, the body and the cap are often formed so as to have different colors. The latter is a dosage form in which a medicine is enveloped with a film formed by adding glycerol or sorbitol to a capsule base (e.g., gelatin) and thereby increasing its plasticity. Soft capsules are classified into capsules formed by sandwiching a medicine between two films and fusing these films together, and seamless capsules formed by dropping solutions or suspensions into a hardening solution through a two-fluid nozzle (see the Pharmacopoeia of Japan, 13th Revised Edition, A-71). Generally, the brief term "capsules" refers to hard capsules in many cases. Also in the present invention, the brief term "capsules" refers to hard capsules.

Generally, capsules are a dosage form gaining the favor of consumers. However, in the early 1980s, an affair in which several persons were killed by a poison added to capsules happened in U.S.A. Since then, consumers' consciousness of safety was raised and the tendency to avoid capsules liable to the addition of a poison has increased. As examples of countermeasures against the addition of a poison, a method of labeling the joint of a capsule with a seal which is broken upon unsealing (U.S. Pat. No. 4,478,658) and a method of using a specially designed packaging material have been proposed. However, all of these countermeasures require an increased cost and, none the less, cannot entirely prevent the addition of a poison.

As a conclusive measure to prevent the addition of a poison, many pharmaceutical makers chose tablets to which a poison in powder form cannot be easily added. Among others, caplets having a long major diameter and hence a shape similar to that of capsules, and film-coated caplets, have found wide acceptance.

In the case of tablets, water-soluble film coating is widely employed for the purpose of masking an unpleasant taste of a drug, stabilizing a drug unstable to light by shielding from light, providing a color coating in order to enhance the identifiability of tablets, or preventing damage to tablets during transportation. Among others, a method using an aqueous solution of hydroxypropyl methylcellulose (HPMC) is most widely employed.

In the early days (1950s) of the development of film coating, the polymerization degree (viscosity) of HPMC used as the base material was high, and organic solvents were used to dissolve it. Thereafter, in the 1970s, the viscosity of the base material was increasingly reduced, and a ventilated pan coater was developed. As a result, the film coating techniques have gradually passed into the use of an aqueous system.

The film-coated tablets thus obtained has a single color, and cannot assume a dual coloration like capsules. However, consumers have a strong demand for capsules. That is, the easy ingestibility of capsules constitutes a psychological factor, and the image of capsules being more efficacious is expected to produce a placebo effect (U.S. Pat. No. 4,820,524). Accordingly, there has been a strong need for the development of preparations having two or more colors like capsules.

With respect to capsule-like preparations, a method of filling caplets, together with an adhesive, into a capsule (U.S. Pat. No. 4,928,840), a method of filling caplets into a capsule in a similar manner and then fitting them together (U.S. Pat. No. 5,511,361), and a method of filling half of the caplets into a capsule and fitting them together (U.S. Pat. No. 5,464,631) have been proposed. Although a capsule-like dual coloration can be realized by these methods, they have the disadvantages that they include troublesome steps and that it is preferable to provide caplets with a film coating in advance and thereby enhance their adhesion to a capsule.

There has also been proposed another method for coating caplets in which caplets are sandwiched between two gelatin films according to the method for the production of soft capsules. Since the tablet surface is coated with gelatin, this method can give a smooth surface and hence excellent ingestibility. However, this method cannot be used to provide tablets with a dual coloration like hard capsules.

Separately from the above-described methods of filling caplets into a capsule, a process for providing caplets with a capsule-like dual coloration by dipping them in a gelatin solution according to the method for the production of capsules (U.S. Pat. No. 4,820,524). This process involves film-coating caplets in advance and dipping them separately in two gelatin solutions having different colors, and requires special equipment similar to the gelatin capsule production equipment. Although this process comprises complicated steps, the resulting caplets can realize a gelatin-coated smooth surface and a capsule-like dual coloration, and have hence achieved a great success in the OTC market.

In order to provide tablets with a dual coloration, there has been proposed a method for producing tablets by preparing two tableting powders having different colors and tableting them according to the method for the production of two-layer tablets (U.S. Pat. No. 5,089,270). However, since this method compresses tablets in their longitudinal direction, the resulting caplets tend to be cracked at the interface between two layers and hence have a problem with strength. Moreover, it is difficult to provide tablets with a coating for improving ingestibility.

In recent years, with an increase in the age of patients, many patients tend to receive treatment for plural diseases, leading to a rise in the number of patients who must take plural tablets prescribed for these diseases. Under such situations, distinguishability of the tablets has been regarded to be very important in order to prevent a mistake not only upon prescription but also upon use by patients.

It is usually said that tablets are desirably distinguished by color, shape or size. Film-coated tablets are, however, in a single color and cannot assume dual coloration like capsules. Hence, they are inferior in distinguishablity to capsules which can assume desirable dual coloration.

In the 1960s of U.S.A., with the spread of prescription of tablets and an increase in the number of tablets taken by one patient, accidents happened frequently owing to a mistake in prescription. Since then, distinguishability of tablets has been carried out widely by employment of color film coating or use of tablets having a shape other than a disk.

On the other hand, in the same period of Japan, carcinogenicity of food colorants became a problem so that many tablets became white, which has lasted up to now. Since patients prefer white, small and disk-shaped tablets, many commercially available tablets are prepared as such. Hence, tablets not only tend to be identified incorrectly at the prescription site but also cause difficulty in medication guidance. Accordingly, there is a strong demand for the improvement of distinguishability of tablets.

As means for improving the distinguishability of tablets, variation in color, shape or size is desired as described above. For example, proposed (U.S. Pat. No. 4,820,524) is a method of imparting caplets with two different colors like capsules by dipping them in a gelatin solution, thereby imparting them with two different colors in accordance with the preparation process of capsules. However, this process needs a special apparatus similar to that for the preparation of gelatin capsules, because caplets which have been film-coated in advance must be dipped twice, more specifically, in two gelatin solutions different in color. This preparation process is thus cumbersome.

It is the common practice to engrave tablets or print the surface of film-coated tablets for improving the distinguishability of film-coated tablets.

Engraved tablets can be easily prepared by conventional film coating, the tablets which have been tableted with a engraved punch in advance. The film-coated tablets thus obtained are in a single color and not always have high distinguishability, however, because the engraving must be recognized from the difference in the brightness between the engraved surface and the rest of the tablet surface. Particularly, engraved tablets which are same in color cannot be distinguished easily. Moreover, symbols or logotypes complicated in shape disturb smooth tableting, thereby markedly shortening the life of the punch so that those usable for engraving are limited. Discrimination by engraving or logotypes involves further many problems such as covering or breaking of the engraved portion by film coating operation or bridging of logotypes.

For identification by printing, tablets are film-coated in a conventional manner, followed by printing. In this case, numerals, engraving or logotypes are printed. However, an increase in the printed area needs long drying time. Another drawback of such identification is that the printed letters become indistinct by rubbing.

As well as engraving or printing, packaging can also be applied to the identification of tablets. In case a package is opened and plural medicaments therein are divided into sub-packages or in other cases, packaging is not effective for identification. Thus its effect is limited.

Use of tablets different in shape does not always bring about an improvement in identifiability, because tableting for smaller and more complex tablets including engraved tablets tends to cause troubles. In addition, the tablets cannot be increased in size freely.

SUMMARY OF THE INVENTION

An object of the present invention is to provide solid preparations having two or more colors which can solve the problems of the prior art including the complexity of production processes and the low strength of solid preparations. Another object of the present invention is to provide film-coated tablets having a pattern of two or more colors, thereby solving the low distinguishability of the prior art.

The present inventors made intensive investigations with a view to solving the above-described problems, and have now found that solid preparations coated with a continuous film coating layer having two or more different colors can be obtained by irradiating a part of the film coating layer containing one or more colorants with light and that the use of these solid preparations can provide, for example, a capsule-like feeling to the throat and a capsule-like appearance, and can provide, for example, a complex logotype engraving. The present invention has been completed on the basis of this finding.

Specifically, the present invention provides a solid preparation coated with a continuous film coating layer having two or more different colors or a pattern of two or more colors wherein the preparation is obtained by irradiating a part of the film coating layer containing one or more colorants with light, a process for the production of such a solid preparation, and a film coating agent therefor. The present invention also provides a solid preparation treating apparatus for imparting two or more different colors or a pattern of two or more different colors to the continuous film coating layer on the surface of a solid preparation, which comprises a solid preparation loader movably disposed, a light controller for controlling the light-exposed surface area of the solid preparation and a light source for irradiation.

By using the solid preparations coated with a continuous film coating layer having two or more different colors which are obtained by irradiating a part of the film coating layer containing one or more colorants with light according to the present invention, it becomes possible to provide, for example, a capsule-like feeling to the throat and a capsule-like appearance.

By using the solid preparations coated with a continuous film coating layer having a pattern of two or more different colors which are obtained by irradiating a part of the film coating layer containing one or more colorants with light according to the present invention, it becomes possible to provide, for example, film-coated tablets having a bar code.

BRIEF DESCRIPTION OF THE DRAWINGS

FIG. 2 include (a) a cross-sectional view illustrating a film-coated tablet 1 in a recess on a rotary drum 2, the rotary drum having a light source 3 at the center thereof; and (b) an enlarged view illustrating the recess portion on the drum in which a tablet is to be set;

DETAILED DESCRIPTION OF THE PREFERRED EMBODIMENTS

The film coating agent of the present invention may comprise any material capable of forming a film layer on the surfaces of tablets and the like. Preferably, there may be used cellulose derivatives which are commonly used as film coating agents. Examples of useful cellulose derivatives include hydroxypropyl methylcellulose (HPMC), methylcellulose (MC) and hydroxypropyl cellulose (HPC). Among others, HPMC and MC are especially preferred.

No particular limitation is placed on the objects coated with the film coating agent of the present invention, provided that they allow a film layer to be formed thereon. They include tablets such as caplets, oblong tablets, round tablets and other irregularly shaped tablets. Among others, caplets and the like are preferred. Although the present invention is described herein chiefly in connection with its application to tablets, it is to be understood that the present invention is not limited thereto.

Such a cellulose derivative is formed into an aqueous solution or an organic solvent solution and sprayed on the surfaces of tablets and the like. In order to achieve an appropriate film strength and an appropriate coating solution concentration, the viscosity of a 2 wt % aqueous solution of the cellulose derivative at 20° C. as described in the Pharmacopoeia of Japan should preferably be in the range of 2 to 18 $mm^2/s$ and more preferably 4 to 8 $mm^2/s$. If the viscosity is less than 2 $mm^2/s$, the degree of polymerization of the cellulose derivative is extremely low, so that the resulting film may not retain a sufficient strength. If the viscosity is greater than 18 $mm^2/s$, it may be necessary to limit the concentration of the aqueous coating solution to a low level unsuitable for practical purposes.

The polymer solution so prepared is sprayed onto the surfaces of tablets and the like by means of a ventilated pan coater or drum type coating apparatus which is commonly used for the manufacture of pharmaceutical preparations. The present invention is especially suitable for the formation of a continuous film coating layer.

The film coating agent of the present invention contains at least one colorants, and a capsule-like dual coloration may be achieved by causing their color to fade as a result of irradiation with light. In other words, the color of the present invention embraces any one of faded, transparent and semi-transparent colors. As the colorants contained in the film coating agent, there may be used any of various colorants approved as food additives. Specific examples thereof include Food Red No. 2 (Amaranth), Food Red No. 3 (Erythrosine), Food Red No. 40 (Aral Red AC), Food Red No. 102 (New Fuchsine), Food Red No. 104 (Phloxine), Food Red No. 105 (Rose Bengal), Food Red No. 106 (Acid Red), Food Yellow No. 4 (Tartrazine), Food Yellow No. 5 (Sunset Yellow), Food Green No. 3 (Fast Green FCF), Food Blue No. 1 (Brilliant Blue FCF) and Food Blue No. 2 (Indigo Carmine). In addition, β-carotene, riboflavin, copper chlorophyllin sodium and the like may also be used. For the purpose of coloring foods and pharmaceutical preparations, aluminum lakes of the foregoing food colors and pigments such as titanium oxide and iron sesquioxide are usually used alone or in admixture. However, it is preferable that the colorants used in the present invention lose their color rapidly by exposure to light. Accordingly, these color lakes and pigments are unpreferable in that they are highly stable to light and their high contents in the film coating agent prevents the transmission of light.

The amount of colorant(s) (a colorant or colorants) contained in the film coating agent may be suitably regulated according to the coating weight. However, it is preferable that the amount of colorant(s) be in the range of 0.001 to 0.5% by weight based on the film coating base material (for example, the cellulose derivative).

In addition, the film coating agent of the present invention may contain one or more selected from other plasticizers and saccharides which are usually added to film coatings.

Useful plasticizers include polyethylene glycol, propylene glycol, glycerol, polyoxyethylene-polyoxypropylene copolymer, triacetin, triethyl citrate and the like. Among them, polyethylene glycol is preferred.

Useful saccharides include monosaccharides, disaccharides, polysaccharides and sugar alcohols, and specific examples thereof include sucrose, sorbitol, lactose, erythritol, mannitol and xylitol.

These plasticizers and saccharides are preferably added in an amount of 5 to 30% by weight based on the film coating base material (for example, the cellulose derivative).

Furthermore, the coating agent may also contain an additive commonly used in coatings, such as an anti-tack agent, an antifoaming agent or perfume.

The coating weight on the solid preparation may vary greatly according to the size and shape of tablets or like objects to be coated. However, for the purpose of coloration aimed at by the present invention, the coating weight should be not less than 0.5% by weight, preferably not less 1% by 410 weight, based on the weight of the object (e.g., tablet) to be coated. If the coating weight on the solid preparation is less than 0.5% by weight, the resulting film may fail to have a sufficiently uniform thickness and hence fade unevenly, resulting in a nonuniform coloration.

As the concentration of the coating solution becomes higher, the tablets can be coated in a shorter time. However, if the coating time is unduly short, a nonuniform coloration tends to occur along the tablet surface and between tablets. For this reason, it is preferable to adjust the concentration of the coating solution according to the desired color and the characteristics of the coating apparatus used. Generally, a concentration of the order of 100 mPa·s may be suitable.

No particular limitation is placed on the type of light used in the present invention, provided that it can promote the color fading of the colorant(s). Although natural light and light from a fluorescent lamp causes the color fading of the colorant(s), they require a long time. Accordingly, it is preferable to use any of various lamps which permit a short-time treatment, as described below.

Although the absorption wavelength pattern may vary with the colorant, light in the ultraviolet region is usually more effective than light in the visible region. Suitable light sources having an intense emission spectrum in the ultraviolet region include, for example, low-pressure mercury lamps used in the fields of photochemical reactions and photosterilization; high-pressure mercury lamps used for the curing of inks, coatings, adhesives and the like; and far-ultraviolet lamps used for the exposure to light of fine circuit patterns on semiconductors and the like. Moreover, xenon lamps and halogen lamps which are used for many purposes as high-brightness light sources can also be utilized because they have a broad emission spectrum and can provide high-power light sources.

The light irradiation step of the present invention may vary according to various factors such as the thickness of the film layer, the concentration of the colorant(s) in the film layer, the type of the colorant(s), the type of the light source, the intensity of the light source, the irradiation conditions, the distance from the light source, and the treating time. However, a practical treating time can be obtained by controlling the intensity of the light source and the distance from the light source.

The present invention is characterized by that a film coating layer has two or more different colors or a pattern of two or more different colors. Examples of the pattern include logotype marks, bar code and letters. Any patterns useful for distinguishing solid preparations may be used. Thus, the pattern can be understood broadly.

The solid preparation treating apparatus used in the present invention has a solid preparation loader movably disposed, a light controller for controlling the light-exposed surface area of the solid preparation and a light source for light irradiation. Preferred is an apparatus having a solid preparation loader movably disposed, conventionally employed printer for solid preparations, light controller for controlling the light-exposed surface area of the solid preparation and a light source for irradiation of light. Such an apparatus can be used in combination with a capsule filling machine. Continuous treatment may be carried out by combination of a capsule filling machine and the solid preparation treating apparatus.

By using such an apparatus, the continuous film coating layer on the surface of the solid preparation is able to have two or more different colors or a pattern of two or more different colors.

Figure 1A:
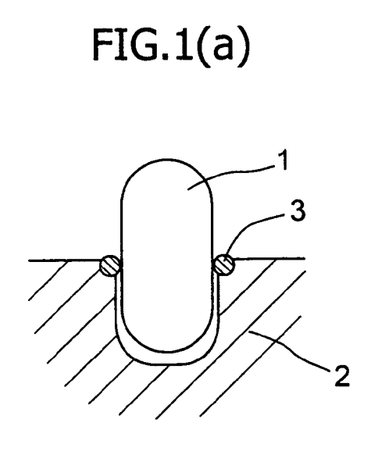
FIG. 1 includes cross-sectional views of film-coated tablets placed in a tray, these views illustrating the use of an O-ring (a) or a flap (b) at the boundary.
Figure 1B:
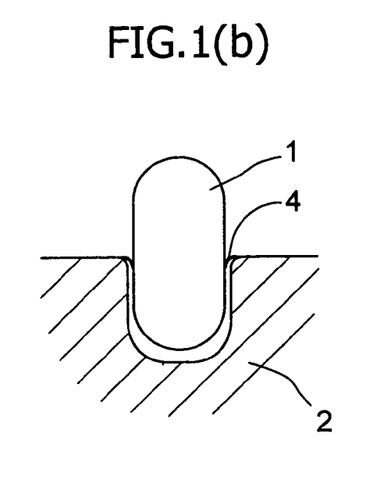

By way of example, in order to obtain a solid preparation having a capsule-like dual coloration, it is necessary to irradiate one half thereof with light while shielding the other half from light. To this end, light must be prevented from leaking through the boundary between the shielded region and the irradiated region, as illustrated in FIGS. 1(a) and 1(b). One preferred method therefor is to place each tablet 1 in a tray 2 having recesses slightly larger than the shielded part thereof and disposing an O-ring 3 or a flap 4 in close contact with the film-coated surface of the tablet. If light leaks, the boundary line between two colors becomes indistinct and thereby impairs the capsule-like appearance of the tablet. The reason why the tray preferably has recesses slightly larger than the shielded part is that the thicknesses of the tablets and the coating film may vary and, therefore, it may be difficult to fit the tablets closely into the recesses.

Figure 2A:
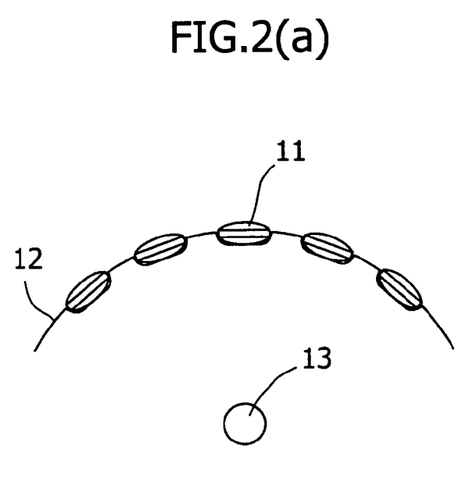
Figure 2B:
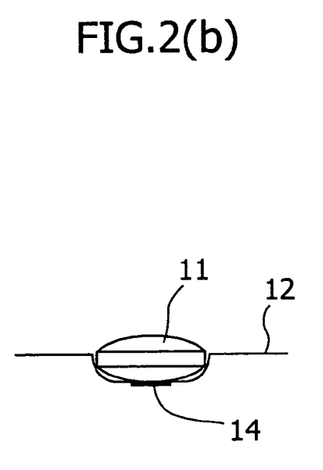

For example, a solid preparation having a bar code has to be prepared by exposing it to light through a photo-mask of a desired pattern (bar code) or a slit. As illustrated in FIG. 2(a) or (b), the rotary drum has a recess for holding the tablet therein and this recess has the photo-mask or slit 14 at the bottom thereof. The light source 13 is disposed inside of the drum. The tablet 11 is exposed to light while being held in the recess 12. For vivid drawing, it is preferred to set the tablet firmly in the recess and to decrease the distance from the mask as much as possible. As a light source, parallel or point light source is preferred. It is possible to keep constant a light angle under irradiation by disposing the light source 3 at the center of the rotary drum.

For example, in the dual coloration, the color of the unirradiated film coating is referred to as A, and the color of the part in which the colorant(s) have been faded by irradiation with light is referred to as B. As the capsule-like dual coloration or a pattern of dual coloration of the present invention, the following combinations are believed to be possible. For example, when white tablets are provided with a film coating containing a red colorant in accordance with the present invention and then irradiated with light to fade the colorant, the resulting tablets are such that A is red and B is white. If tablets are previously color-coated by applying thereto a yellow coating having a high pigment content, and then treated in the same manner as described above, the resulting tablets are such that A is red and B is yellow.

The following is an example of preparing tablets having a bar code as a pattern. When white tablets are subjected to coating with a film containing a red colorant by using a photo-mask which permits passage of light at the portion of a bar code and then exposed to light to cause fading of the colorant, the resulting tablets are such that A is red and B (bar code) is white. If tablets are previously color-coated by applying thereto a black coating having a high pigment content, and then treated in the same manner as described above, the resulting tablets are such that A is red and B is black.

Moreover, if tablets are colored in blue during their preparation (for example, by coloring the binder solution used during granulation), and then treated in the same manner as described above, the resulting tablets are such that A is red and B is blue. Thus, A is defined by the colorant(s) incorporated into the film coating, while B is the color of the substrate as seen through the faded transparent film coating. The color of the substrate may be the color of the tablet or the color of a film coating layer formed from a composition having a high content of a color lake or pigment having high resistance to irradiation with light. Thus, there may be obtained any desired combination of two or more colors.

If the drug used has poor stability to light, light resistance can be imparted thereto by increasing the amount of a prime coating containing a pigment as described above.

Where the color of the tablet is used as the color of the substrate, this may be done by incorporating a fade-resistant color lake or pigment into the binder solution used for the granulation of the tableting powder as described above, or by dry-blending a color lake or pigment directly with the tableting powder.

Where the color of a prime film coating is used as the color of the substrate, the prime film coating may be formed in the same manner as in the practice of the present invention, by using a ventilated pan coater or drum type coating apparatus which is commonly used in the manufacture of pharmaceutical preparations. Accordingly, the color coating of the present invention may be continuously carried out after the prime coating.

Figure 3:
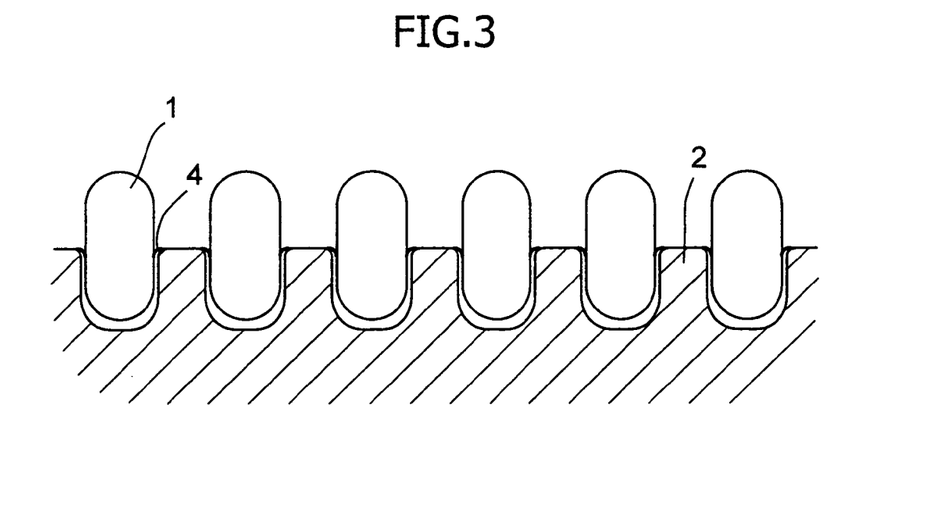
FIG. 3 is a cross-sectional view of film-coated tablets arranged in a tray.

After the tablets provided with a film coating containing one or more colorants are prepared in the above-described manner, they are placed in recoverable recesses having a size slightly larger than the shielded part thereof, for example, by using a mechanism similar to a capsule filling machine as illustrated in FIG. 3, and then passed through a lamp box in a predetermined time. Thus, there are obtained film-coated tablets having a capsule-like dual coloration in accordance with the present invention. As compared with the method of dipping in a gelatin solution or the like, this method is characterized in that no drying step is required and a large quantity of tablets can be treated in a shorter time.

Figure 4:
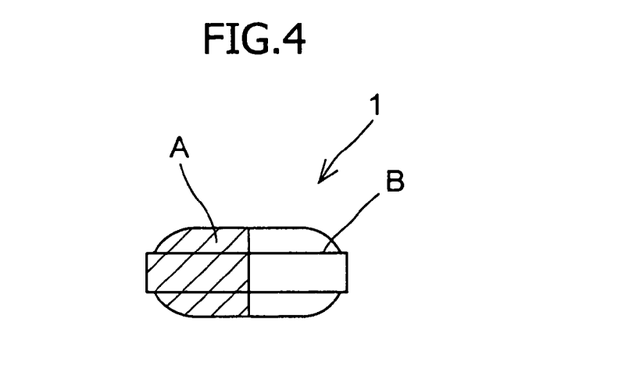
FIG. 4 is a coated tablet as prepared in any of Examples 1 to 3.

After the tablets coated with a film containing one or more colorants are prepared in the above-described manner, they are placed in recesses by using a mechanism similar to a capsule filling machine as illustrated in FIG. 4 and then exposed to light in a predetermined time. Thus, there are obtained film-coated tablets of the present invention having two or more different colors or a pattern of two or more different colors. As compared with the conventional printing method, this method is characterized in that a drying step or like is not necessary and a large quantity of tablets can be treated in a shorter time. In addition, even direct rubbing does not blur or smear the pattern.

The film-coated tablets thus obtained may further be polished to impart a gloss thereto, or provided with an enteric coating so as to be disintegrable in the intestines.

In order to obtain tablets having a satisfactory capsule-like appearance as aimed at by the present invention, they preferably comprise caplets having an oblong shape. However, by applying the present invention to tablets having a common shape, there can be obtained film-coated tablets having different colors on the opposite sides and hence excellent identifiability.

In the practice of the present invention, a bar code can be depicted by shielding the colorant-containing film coating layer from light with the aid of a slit.

Furthermore, any desired pattern can be depicted by using, upon shielding the colorant-containing film coating layer from light, a photomask similar to the circuit patterns used in the semiconductor industry. For example, if characters are used in the photomask, it can be expected to achieve exactly the same effect as the printing on film-coated tablets which is commonly practiced in the manufacture of pharmaceutical preparations. Moreover, this technique enables very small characters to be depicted, in contrast to conventional printing techniques in which it has been difficult to print them. The same is also true in comparison with engraved tablets. Similar effects to photography may be given if gradation is employed for this mask pattern. For example, highly-designed film-coated tablets on which figures or landscape has been drawn like the surface of a coin can be obtained. The patterns thus obtained have the advantage that they are scarcely blurred or smeared even if they are directly rubbed, as compared with those obtained by conventional printing means and the like.

The present invention is more specifically explained with reference to the following examples. However, it is to be understood that the present invention is not limited to the details of these examples.

Example 1

(Coating)

A coating solution was prepared by dissolving 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 1 part by weight of polyethylene glycol (Macrogol 6000P, manufactured by Nippon Oil & Fats Co., Ltd.), and 0.12 part by weight of Food Red No. 3 (manufactured by Daiwa Chemical Co., Ltd.) in 92.88 parts by weight of purified water.

A small-sized ventilated pan coater (manufactured by Shin-Etsu Chemical Co., Ltd.) was charged with 1.2 kg of white caplets (each weighing 450 mg) formed principally of lactose and having a major diameter of 15 mm and a minor diameter of 6.5 mm. At a feed air temperature of 80° C., the coating solution was sprayed at a rate of 6 g per minute to obtain coated caplets having a coating weight of 9 mg per caplet.

(Irradiation with Light)

As illustrated in FIG. 3, tablets 1 obtained as described above were placed in a tray 2 having recesses slightly larger than the shielded part. Then, using a lamp house in which several high-pressure mercury lamps (UM-452, manufactured by Ushio Inc.) were used in a row as light sources, the tablets were irradiated with ultraviolet light for 30 minutes at a distance of 10 cm from the light sources.

As illustrated in FIG. 4, the resulting tablets assumed a capsule-like coloration in which the part B irradiated with light was white and the unirradiated part A was red.

Example 2

(Coating)

A prime coating solution was prepared by dissolving or dispersing 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 2 parts by weight of polyethylene glycol (Macrogol 6000P, manufactured by Nippon Oil & Fats Co., Ltd.), 0.6 part by weight of Food Yellow No. 4 aluminum lake (manufactured by Daiwa Chemical Co., Ltd.), and 0.3 part by weight of titanium oxide (A-110, manufactured by Sakai Chemical Industry Co., Ltd.) in 91.1 parts by weight of purified water.

This prime coating agent was used in the same manner as in Example 1 to obtain coated tablets having a coating weight of 18 mg per tablet.

Subsequently, these tablets were provided with the red coating of Example 1 under the same conditions as described in Example 1.

(Irradiation with Light)

The tablets so treated were irradiated with ultraviolet light under the same conditions as described in Example 1.

As illustrated in FIG. 4, the resulting tablets assumed a capsule-like coloration in which the part B irradiated with light was yellow and the unirradiated part A was red.

Example 3

(Coating)

A coating solution was prepared by dissolving 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 1 part by weight of polyethylene glycol (Macrogol 6000P, manufactured by Nippon Oil & Fats Co., Ltd.), and 0.012 part by weight of Food Blue No. 1 (manufactured by Daiwa Chemical Co., Ltd.) in 92.988 parts by weight of purified water.

This coating solution was sprayed onto tablets in the same manner as in Example 1 to obtain coated tablets having a coating weight of 14 mg per tablet.

(Irradiation with Light)

The tablets so treated were irradiated with ultraviolet light under the same conditions as described in Example 1.

As illustrated in FIG. 4, the resulting tablets assumed a capsule-like coloration in which the part B irradiated with light was white and the unirradiated part A was blue.

The results thus obtained are summarized in Table 1.

TABLE 1

|  | Unirradiated part (A) | Part irradiated with light (B) |
| --- | --- | --- |
| Example 1 | Red | White |
| Example 2 | Red | Yellow |
| Example 3 | Blue | White |

Example 4

(Coating)

A coating solution was prepared by dissolving 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 1 part by weight of polyethylene glycol (Macrogol 6000P, manufactured by Nippon Oil & Fats Co., Ltd.), and 0.12 part by weight of Food Red No. 3 (manufactured by Daiwa Chemical Co., Ltd.) in 92.88 parts by weight of purified water.

A small-sized ventilated pan coater (manufactured by Shin-Etsu Chemical Co., Ltd.) was charged with 1.2 kg of white tablets (each weighing 450 mg) formed principally of lactose and having a diameter of 10 mm. At a feed air temperature of 80° C., the coating solution was sprayed at a rate of 6 g per minute to obtain coated caplets having a coating weight of 9 mg per tablet.

(Irradiation with Light)

Figure 5:
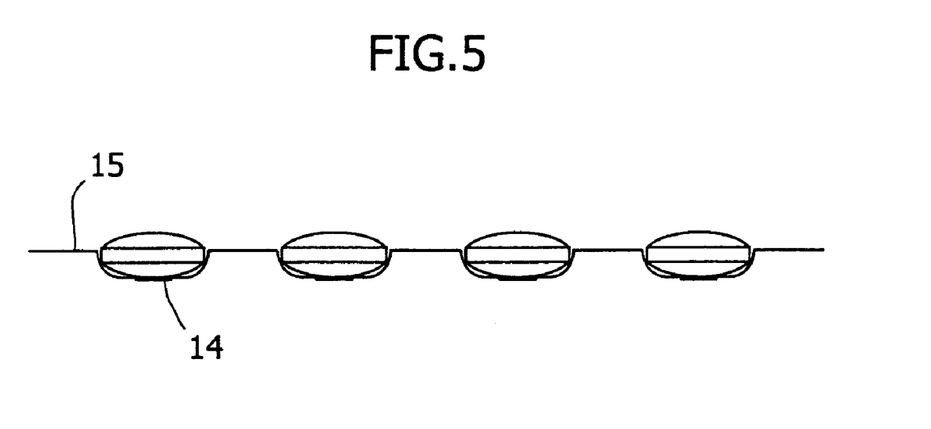
FIG. 5 is a cross-sectional view of film-coated tablets arranged in a row on the tray which has a slit or photo mask at the bottom thereof.

As illustrated in FIG. 5, tablets 1 obtained as described above were placed in a tray 15 having recesses. Then, in a lamp house in which a ultrahigh-pressure mercury lamp (USH-500D, manufactured by Ushio Inc.) was disposed as a light source, the tablets were exposed to ultraviolet light for 1 minute at a distance of 10 cm from the light source.

Disposed at the bottom 14 of the recess was a photo-mask permitting permeation of light at the bar code portion.

Figure 6:
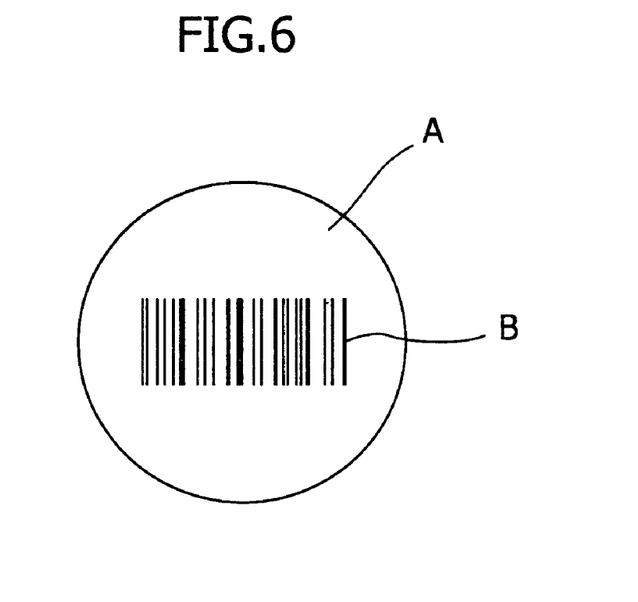
FIG. 6 illustrates coated tablets obtained in any of Examples 4 to 6.

As illustrated in FIG. 6, the light-irradiated portion B of the resulting tablets was white, while the nonirradiated portion A was imparted with a red bar code.

Example 5

(Coating)

A prime coating solution was prepared by dissolving or dispersing 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 2 parts by weight of polyethylene glycol (Macrogol 6000P, manufactured by Nippon Oil & Fats Co., Ltd.), and 0.9 part by weight of black iron oxide (manufactured by Nippon Karacon Co., Ltd.) in 91.1 parts by weight of purified water.

In a similar manner to Example 4, coated tablets having a coating weight of 18 mg per tablet were obtained. The resulting tablets were subjected to red coating as described in Example 4 under similar conditions to Example 4.

(Irradiation with Light)

The tablets thus obtained were exposed to ultraviolet light under similar conditions to Example 4.

As illustrated in FIG. 6, the light-irradiated portion B of the resulting tablets was black, while the nonirradiated portion A was imparted with a red bar code.

Example 6

(Coating)

A coating solution was prepared by dissolving 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 1 part by weight of polyethylene glycol (Macrogol 6000P, manufactured by Nippon Oil & Fats Co., Ltd.), and 0.012 part by weight of Food Blue No. 1 (manufactured by Daiwa Chemical Co., Ltd.) in 92.988 parts by weight of purified water.

In a similar manner to Example 4, the coating solution was sprayed and coated tablets, as illustrated in FIG. 6, having a coating weight of 14 mg per tablet were prepared.

(Irradiation with Light)

The tablets thus obtained were exposed to ultraviolet light under similar conditions to Example 4.

As illustrated in FIG. 6, the light-irradiated portion B of the resulting tablets was white, while the nonirradiated portion A was imparted with a blue bar code.

Example 7

(Coating)

A coating solution was prepared by dissolving 6 parts by weight of low-viscosity hydroxypropyl methylcellulose (TC-5R, manufactured by Shin-Etsu Chemical Co., Ltd.; a 2 wt % aqueous solution thereof having a viscosity of 5.8 mm$^2$/s at 20° C.), 1 part by weight of polyethylene glycol (Macrogol 6000P, manufactured by Nippon Oil & Fats Co., Ltd.), 0.20 part by weight of Food Red No. 40 (manufactured by Daiwa Chemical Co., Ltd.) and 0.06 part by weight of Food Blue No. 1 (manufactured by Daiwa Chemical Co., Ltd.) in 92.74 parts by weight of purified water.

A small-sized ventilated pan coater (manufactured by Shin-Etsu Chemical Co., Ltd.) was charged with 1.2 kg of white tablets (each weighing 450 mg) formed principally of lactose and having a diameter of 10 mm. At a feed air temperature of 80° C., the coating solution was sprayed at a rate of 6 g per minute to obtain coated tablets having a coating weight of 13.5 mg per tablet.

(Irradiation with Light)

Under similar conditions to Example 4, tablets obtained as described above were exposed to ultraviolet light by using a portrait (a mask with gradation permitting permeation of light through the bright part of the face) as a photo-mask.

The tablets thus obtained had, on the surface film thereof, a cameo-like pattern wherein a white figure stood out in relief against a grape color.

The invention claimed is:

1. A solid preparation coated with a multi-colored continuous film coating layer, prepared by the process of
    coating a solid preparation with a continuous film coating layer having one or more colorants; and,
    exposing a first part of the coating layer to a first amount of radiation and exposing a second part of the coating layer to a second amount of radiation under conditions sufficient to result in the first and second parts of the coating layer having different coloration, and wherein said film coating layer has a pattern of two or more different colors comprising a logo.

2. The solid preparation of claim 1, wherein said solid preparation is a tablet.

3. The solid preparation of claim 1, wherein said continuous film coating layer comprises one or more cellulose derivatives as film coating agents.

4. The solid preparation of claim 3, wherein said cellulose derivative is selected from the group consisting of hydroxypropyl methyl cellulose (HPMC), methylcellulose (MC) and hydroxypropyl cellulose (HPC).

5. The solid preparation of claim 4, wherein said cellulose derivative is hydroxypropyl methyl cellulose.

6. The solid preparation of claim 1, wherein at least a portion of said film is exposed to radiation under conditions sufficient to fade the exposed colorant.

7. The solid preparation of claim 1, wherein at least a portion of said film is exposed to radiation under conditions sufficient to render the exposed colorant semi-transparent.

8. The solid preparation of claim 1, wherein said colorant is a food additive.

9. The solid preparation of claim 1, wherein said solid preparation further comprises at least one additional layer underlying said continuous film coating layer, said at least one additional layer comprising a colorant to impart a color thereto that is different from the colors of the overlying continuous film coating layer.

10. A solid preparation coated with a multi-colored continuous film coating layer, prepared by the process of
    coating a solid preparation with a continuous film coating layer having one or more colorants; and,
        exposing a first part of the coating layer to a first amount of radiation and exposing a second part of the coating layer to a second amount of radiation under conditions sufficient to result in the first and second parts of the coating layer having different coloration, and wherein said film coating layer has a pattern of two or more different colors comprising a bar code.

11. A solid preparation coated with a multi-colored continuous film coating layer, prepared by the process of
    coating a solid preparation with a continuous film coating layer having one or more colorants; and,
        exposing a first part of the coating layer to a first amount of radiation and exposing a second part of the coating layer to a second amount of radiation under conditions sufficient to result in the first and second parts of the coating layer having different coloration, and wherein said film coating layer has a pattern of two or more different colors comprising letters.

12. The solid preparation of claim 1, wherein at least a portion of said film coating layer is exposed to radiation under conditions sufficient to render the exposed colorant transparent.

13. A solid preparation coated with a multi-colored continuous film coating layer, prepared by the process of
    coating a solid preparation with a continuous film coating layer having one or more colorants; and,
        changing the coloration of one or more parts of the coating layer by irradiating those parts of the coating layer to the exclusion of the remainder of the coating, and wherein said film coating layer has a pattern of two or more different colors selected from the group consisting of a logo a bar code, and letters.

14. The solid preparation of claim 13, wherein said pattern comprises a bar code.

15. The solid preparation of claim 13, wherein said pattern comprises letters.

16. The solid preparation of claim 13, wherein said solid preparation is a tablet.

17. The solid preparation of claim 13, wherein said continuous film coating layer comprises one or more cellulose derivatives as film coating agents.

18. The solid preparation of claim 17, wherein said cellulose derivative is selected from the group consisting of hydroxypropyl methyl cellulose (HPMC), methylcellulose (MC) and hydroxypropyl cellulose (HPC).

19. The solid preparation of claim 18, wherein said cellulose derivative is hydroxypropyl methyl cellulose.

20. The solid preparation of claim 13, wherein at least a portion of said film is exposed to radiation under conditions sufficient to fade the exposed colorant.

21. The solid preparation of claim 13, wherein at least a portion of said film is exposed to radiation under conditions sufficient to render the exposed colorant transparent.

22. The solid preparation of claim 13, wherein at least a portion of said film is exposed to radiation under conditions sufficient to render the exposed colorant semi-transparent.

23. The solid preparation of claim 14, wherein said colorant is a food additive.

24. The solid preparation of claim 13, wherein said solid preparation further comprises at least one additional layer underlying said continuous film coating layer, said at least one additional layer comprising a colorant to impart a color thereto that is different from the colors of the overlying continuous film coating layer.

* * * * *